United States Patent
Rabinovitz et al.

(10) Patent No.: US 10,441,766 B2
(45) Date of Patent: Oct. 15, 2019

(54) METHOD FOR CLEARING A BODY LUMEN ENVIRONMENT

(71) Applicant: GIVEN IMAGING LTD., Yoqneam (IL)

(72) Inventors: Elisha Rabinovitz, Haifa (IL); Daniel Gat, Zichron Yaakov (IL); Shirrie Rosenthal, Zerufa (IL)

(73) Assignee: GIVEN IMAGING LTD., Yoqneam (IL)

( * ) Notice: Subject to any disclaimer, the term of this patent is extended or adjusted under 35 U.S.C. 154(b) by 564 days.

(21) Appl. No.: 13/803,693

(22) Filed: Mar. 14, 2013

(65) Prior Publication Data

US 2013/0204086 A1   Aug. 8, 2013

Related U.S. Application Data

(63) Continuation-in-part of application No. 12/672,228, filed as application No. PCT/IL2008/001094 on Aug. 7, 2008, now abandoned.

(60) Provisional application No. 60/935,345, filed on Aug. 8, 2007.

(51) Int. Cl.
| | | |
|---|---|---|
| A61M 37/00 | (2006.01) | |
| A61B 1/04 | (2006.01) | |
| A61B 1/31 | (2006.01) | |
| A61B 5/00 | (2006.01) | |
| A61M 31/00 | (2006.01) | |

(52) U.S. Cl.
CPC .............. *A61M 37/00* (2013.01); *A61B 1/041* (2013.01); *A61B 1/31* (2013.01); *A61B 5/0084* (2013.01); *A61B 5/6861* (2013.01); *A61M 31/002* (2013.01)

(58) Field of Classification Search
CPC ......... A61B 5/6861; A61B 1/31; A61B 1/041; A61B 1/0684; A61B 5/4255; A61B 5/42; A61M 37/00; A61M 31/002
See application file for complete search history.

(56) References Cited

U.S. PATENT DOCUMENTS

| | | | |
|---|---|---|---|
| 5,486,154 A | 1/1996 | Kelleher | |
| 6,866,873 B2 * | 3/2005 | Stern | A23L 2/52 424/725 |
| 7,009,634 B2 | 3/2006 | Iddan et al. | |
| 7,192,397 B2 | 3/2007 | Lewkowicz et al. | |
| 2002/0146368 A1 * | 10/2002 | Meron et al. | 424/1.49 |
| 2002/0198470 A1 * | 12/2002 | Imran et al. | 600/587 |
| 2005/0143623 A1 | 6/2005 | Kojima | |
| 2005/0177069 A1 | 8/2005 | Takizawa et al. | |

(Continued)

FOREIGN PATENT DOCUMENTS

| | | | |
|---|---|---|---|
| WO | WO 2006/070378 | 7/2006 | |
| WO | WO 2006070378 A2 * | 7/2006 | A61B 1/273 |

OTHER PUBLICATIONS

International Search Report for International Application No. PCT/IL2008/001094 dated Jan. 21, 2009.

*Primary Examiner* — Bhisma Mehta
*Assistant Examiner* — Hamza A Darb
(74) *Attorney, Agent, or Firm* — Pearl Cohen Zedek Latzer Baratz LLP

(57) ABSTRACT

An in vivo sensing device and system may contain or be used in conjunction with an image sensor and a body lumen clearing element or agent. A method may enable clearing a body lumen for in vivo sensing while using the device of the invention.

14 Claims, 3 Drawing Sheets

(56) References Cited

U.S. PATENT DOCUMENTS

2005/0192478 A1    9/2005   Williams et al.
2006/0121067 A1*   6/2006   Hamawaki ........... A61K 9/1075
                                                                     424/400
2006/0233941 A1    10/2006   Olson

* cited by examiner

METHOD FOR CLEARING A BODY LUMEN ENVIRONMENT

CROSS REFERENCE TO RELATED APPLICATIONS

This application is a Continuation-in-Part of U.S. patent application Ser. No. 12/672,228, which was filed on Feb. 4, 2010, which is a National Phase Application of PCT International Application No. PCT/IL2008/001094, International Filing Date Aug. 7, 2008, which claims priority from U.S. Provisional patent application No. 60/935,345, which was filed on Aug. 8, 2007, which is hereby incorporated by reference in its entirety.

FIELD OF THE INVENTION

The present invention relates to in-vivo imaging and to a method, device, and system for clearing a body lumen for in-vivo imaging.

BACKGROUND OF THE INVENTION

When viewing a body lumen, for example the gastrointestinal (GI) tract, turbidity may reduce image quality.

For example, an in-vivo imager system which is carried by an ingestible capsule may be used to image lumens within a patient. The imager system may capture and transmit, for example, images of the gastrointestinal (GI) tract to an external recording device while the in-vivo device passes through the GI lumen.

Such an in-vivo imaging system provides a platform from which moving or still images of a lumen may be viewed. An ingestible capsule may pass through different portions of the GI tract which may vary in their structure and content. For example, turbidity and hence the visibility, may differ between the small intestine and the colon.

Poorly visualized mucosa caused by luminal particles and/or bubbles may lead to poor visualization and/or missed diagnoses. Consequently proper body lumen examination is desirable and may require a clean luminal environment.

Colonoscopy is a medical procedure during which a long, flexible, tubular instrument called the colonoscope is used to view typically the entire inner lining of the colon and the rectum. Colonoscopy is frequently used to test for colorectal cancer, especially when polyps or tumor-like growths have been detected using for example barium enema and other diagnostic tests. Bowel cleaning preparation typically precedes colonoscopy and may be tiring and produce diarrhea and cramping. Most patients complain of discomfort during and after such preparations. Patient compliance in colorectal cancer screening is somewhat compromised.

Therefore, a need exists for an in-vivo device, system and method which enables a viewer to examine or record images of a body lumen in a range of conditions that may be influenced by luminal content while reducing the discomfort associated with cleaning preparation.

SUMMARY OF THE INVENTION

One embodiment of the invention includes an in-vivo sensing device containing an image sensor or other suitable sensor; and a body lumen clearing element.

Another embodiment of the invention provides a method for clearing a body lumen for in-vivo sensing including for example administering to a subject an in-vivo sensing device and administering a composition containing a lumen clearing element.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
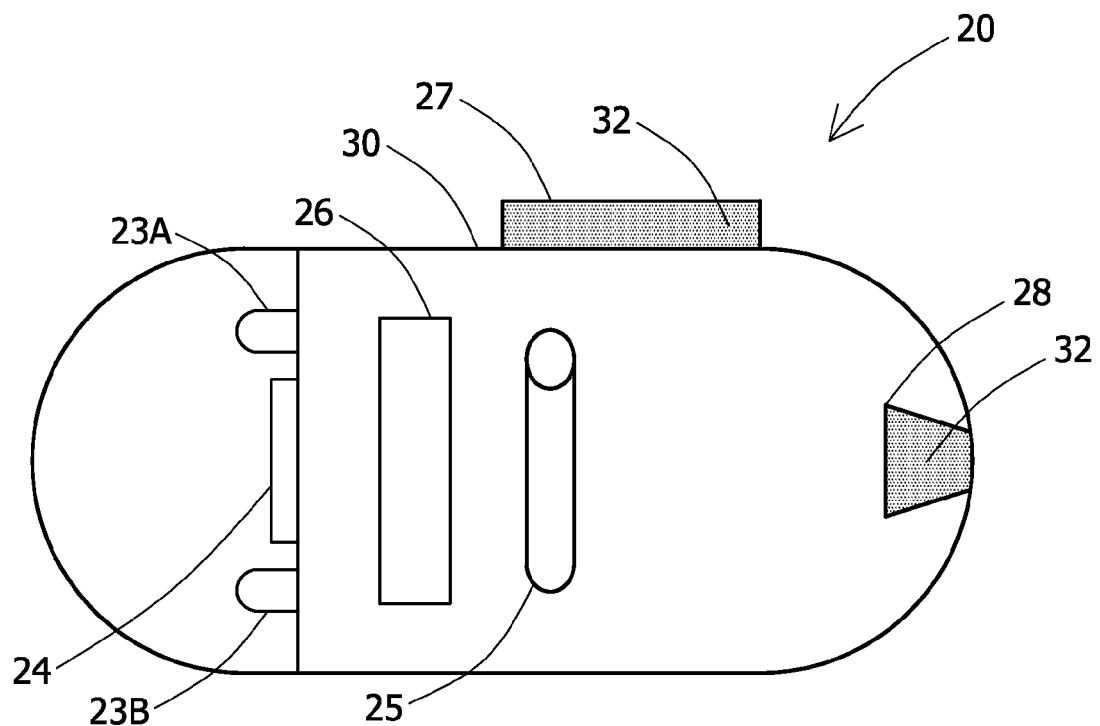
FIG. 1 is a schematic illustration of an in-vivo device according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the present invention may enable viewing a body lumen by diagnostic and/or therapeutic sensing devices, such as a swallowable imaging capsule, an endoscope, a colonoscope and other intra luminal viewing and imaging devices. Viewing may be facilitated, through, for example, clearing a turbid or otherwise occluded or unclear body lumen environment. Such clearing may include removing or causing the settling out of content via a clearing element or agent. Such clearing may be performed exclusively by or may be facilitated by a clearing element or agent administered with or in conjunction with an in-vivo imaging or sensing device, Such clearing may substitute for, or may augment, traditional clearing or colon prep procedures.

An in-vivo device 20 in accordance with an embodiment of the invention is schematically illustrated in FIG. 1. In-vivo device 20 may be or may include an autonomous swallowable capsule, but in-vivo device 20 may have other shapes and need not be swallowable or autonomous. Embodiments of in-vivo device 20 are typically autonomous, and are typically self-contained. For example, a swallowable capsule may be similar to the embodiments described in U.S. Pat. No. 7,009,634 to Iddan et al. and U.S. Pat. No. 7,192,397 to Lewkowicz et al. both of which are incorporated herein by reference, but other structures and elements may be used. A reception system and a display system may also be similar to those described in U.S. Pat. Nos. 7,009,634 and 7,192,397. The in-vivo device 20 may be similar to systems other than described in U.S. Pat. Nos. 7,009,634 and 7,192,397.

In an exemplary embodiment, the in-vivo device 20 includes an illumination unit, typically including one or more illumination source(s) such as white LEDs 23A and 23B, an image sensor 24, and a transmitter 26 for transmitting image signals of image sensor 24. In-vivo device 20 may communicate with an external receiving and display system to provide display of data, control, or other functions. In-vivo device 20 may include a body lumen clearing element cavity or reservoir 28 or a coated body lumen clearing element 27. The in-vivo device may contain a power source 25, such as a silver oxide battery. For example, in an autonomous system power may be provided by an internal battery or a wireless receiving system. A container or shed 30 encapsulates the components of in-vivo device 20 and may include more than one piece. For example, a plastic shell 30 may include an opaque portion which is cylindrical with a rounded cap at one end and a clear plastic or glass cap at another end. The transmitter 26 may be for example a radio frequency ("RF") transmitter. Other components and configurations of components may be used; for example the illumination sources need not be white LEDs. Reservoir 28 or coating 27 may include a body lumen clearing element 32 such as that described herein. A sensor other than or in addition to an image sensor may be used.

Typically, in-vivo device 20 is swallowed by a patient and traverses the patient's GI tract; however, other body lumens or cavities may be imaged or examined. The in-vivo device 20 transmits image and/or other data to components located outside the patient's body which receive and process the data.

Figure 2:
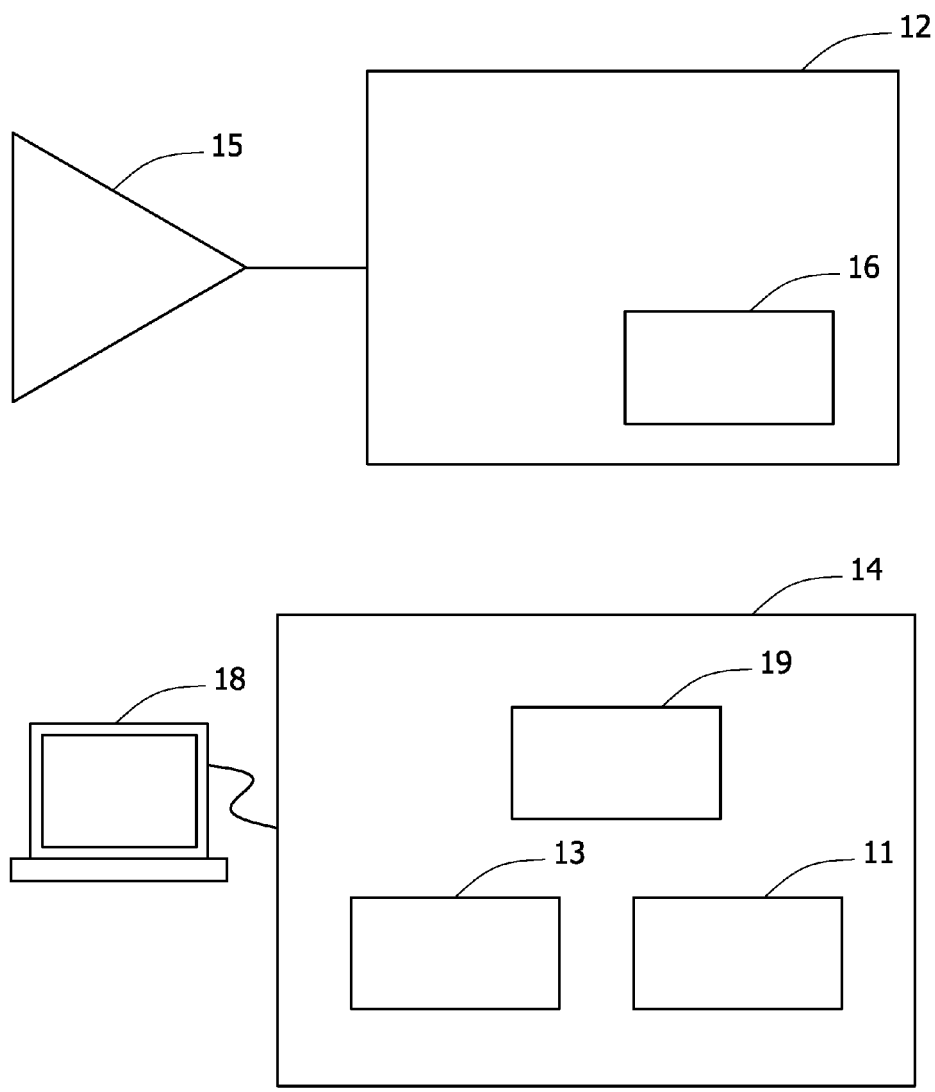
FIG. 2 is a schematic illustration of a system according to an embodiment of the invention.

FIG. 2 depicts a receiving and a display system according to an embodiment of the present invention. Typically, located outside the patient's body in one or more locations, are a receiver 12, typically including an antenna 15 or antenna array, for receiving image and possibly other data from in-vivo device 20, a receiver storage unit 16, for storing image and other data, a data processor 14, a data processor storage unit 19, a graphics unit 11, and an image monitor 18, for displaying, inter alia, the images transmitted by the in-vivo device 20 and recorded by the receiver 12. Typically, the receiver 12 and receiver storage unit 16 are small and portable, and are worn on the patient's body during recording of the images.

Typically, data processor 14, data processor storage unit 19 and monitor 18 are part of a personal computer or workstation which includes standard components such as a processor 13, a memory (e.g., storage 19, or other memory), a disk drive, and input-output devices, although alternate configurations are possible. Typically, in operation, image data is transferred to the data processor 14, which, in conjunction with processor 13 and software, stores, possibly processes, and displays the image data on monitor 18. Graphics unit 11 may, inter alia, form color images, and may perform other functions. Graphics unit 11 may be implemented in hardware or, for example, in software, using processor 13 and software. Graphics unit 11 need not be included, and may be implemented in other manners.

In alternate embodiments, the data reception and storage components may be of another configuration, and other systems and methods of storing and/or displaying collected image data may be used. Further, image and other data may be received in other manners, by other sets of components.

Coating 27 may be for example a layer on the outside of the container or shell 30 of in-vivo device 20. Coating 27 may extend to other portions of shell 30 than shown in FIG. 1, and the in-vivo device 20 may have other shapes. Reservoir 28 may be housed within an in-vivo device 20 and may have an opening to the outside of shell 30. A substance within reservoir 28 may be released by any appropriate method such as by a valve, pump, or by for example a dissolvable plug. Other methods or devices for dispensing a body lumen clearing element 32 from an in-vivo device 20 may be used. Typically either coating 27 or reservoir 28 is used, or another method for introducing a clearing element is used, but in some embodiments a combination of such elements may be used.

The in-vivo device 20 is typically capsule shaped, and typically can be easily swallowed and may passively pass through the entire GI tract. However, other shapes and configurations may be used. While the in-vivo device 20 is administered or inserted into the body by swallowing in one embodiment, other methods of administration may be used. While passing through tube-like portions of the GI tract, such as the small intestine, the in-vivo device 20 may be pushed along by natural peristalsis and may be restricted by the tube walls to a fixed orientation. As the in-vivo device 20 passes through the small intestine it may periodically image the tube wall. However, when the in-vivo device 20 reaches cavities such as the stomach or the large intestine it may not be restricted by the lumen walls and it may, for example, rotate and tumble through the lumen.

In-vivo device 20 may include, a body lumen clearing element 32 possibly coating 27 or reservoir 28; a lumen clearing component may be located on another part of the in-vivo device 20 or may be administered to a patient separately from a device 20. Body lumens may include for example the GI tract, blood vessels, lymphatic vessels, the reproductive tract, the respiratory tract, the urinary tract or any other suitable body lumens. The body lumen clearing element may be for example a chemical compound such as a coagulant. A chemical compound carrier moiety may be used as would be readily evident to one skilled in the art of the. Additionally, a body lumen clearing element may include a combination of chemical compounds.

Clearing a body lumen for in-vivo imaging or sensing using for example in-vivo device 20 may include according to some embodiments separation of solid luminal particles from luminal fluids. Separation of luminal solid particles and luminal fluids may reduce the need to place a patient on for example gut lavage, application 110 and/or 120. Clearing using a clearing agent such as clearing agent 32 may reduce or eliminate traditional colon prep procedures.

According to some embodiments flocculating agents may be used. Floating particles or other particles in a turbid media may agglomerate around the flocking agent and then settle, thus leaving in the lumen a clear media.

Flocculating agents may be administered in powder form or in any other suitable form. Flocked particles may leave the body naturally or may be washed out, for example by using traditional colon prep procedures.

Typically, imaging or sensing using devices such as device 20 do not require body lumen insufflation. The reduction or elimination of colon prep procedures combined with the elimination of insufflation may provide a much more comfortable procedure for patients.

Coagulants may serve, in some embodiments, as a body lumen clearing agent 32. The use of coagulants may provide sufficient clarity for in-vivo device 20. Coagulants may separate floating particles from luminal liquid. Hence, sufficiently clearing a body lumen by precipitating the luminal particles may be facilitated by coagulants which may act as particle absorbers. Other luminal particles absorbing agents may be used. In some embodiments, the use of coagulants may reduce the discomfort associated with cleansing procedures that may precede colonoscopy.

Other extremely porous materials, formed as beads for example, may serve in some embodiments as a body lumen clearing agent. Porous beads, such as activated carbon, have a very large surface area available for adsorption or chemical reactions and thus can adsorb luminal particles. The colloids formed may leave the body naturally or may be washed out, for example by using traditional colon prep procedures.

Ion or Cation-Exchange Resins, either natural or synthetic, may serve in some embodiments, as a body lumen clearing agent. Ion-Exchange Resins are typically derivatized to contain covalently linked positively or negatively charged groups. Floating particles from the luminal liquid may bind through electrostatic interactions to the charged group on the resin, thus forming flocs that may be eliminated naturally, or may be washed out.

Examples of such resins are Bile Acid Sequestrants, e.g., Cholestyramine and Chitosan, which is a derivative of Chitin.

In some embodiments, the body lumen clearing element includes a chemical such as sodium phosphate monobasic, monohydrate and sodium phosphate dibasic, or anhydrous or sodium picosulphate.

In some embodiments, the body lumen clearing agent includes senna, Bisacodyl, PEG-ELS, or SF-ELS. PEG-ELS or SF-ELS, and may be formulated in a powder form.

In some embodiments, the body lumen clearing agent includes Aluminum Hydroxide. In some embodiments, the body lumen clearing agent includes surface treated Diatomaceous Earth (DE) with Eudragil® RL-30D by Evonik Industries AG, Germany. An example for preparation of surface treated Diatomaceous Earth with Eudragit® RL-30D, which may be used as part of a body lumen clearing agent may include adding 1583.3 gr Ethanol to 232.2 gr Eudragit® RL-30Dsolids in order to reduce the Eudragit® RL-30Dsolids to approximately 5.0%. Then 110.4 gr Diatomaceous Earth may be added to the Eudragit® RL-30D solution. Following filtration and drying of the solution 180.0 gr of solids is prepared for use as part of a body lumen clearing agent. Other ratios and combinations of Eudragit® RL-30D, Diatomaceous Earth, and/or Ethanol may also be used.

In some embodiments, administering of an in-vivo device 20 including a coating 27 or reservoir 28 may require administering of water in volumes that would be readily evident to one skilled in the art.

The lumen clearing agent may act, for example, to clear the lumen of most solid and liquid matter. For example, isotonic solutions may be utilized for body lumen cleansing. A body lumen clearing element of an embodiment of the invention may clear a turbid or otherwise occluded lumen allowing the in-vivo device to have a clearer view of the lumen for example including the lumen walls.

The lumen-clearing agent 32 may be part of a coating such as coating 27. The term "coating" may refer to an application where the compound remains in association with at least a portion of a surface of a device, for a period of time, which may range from seconds to hours, as will be suitable for a given application.

The in-vivo device 20 housing may be coated by various suitable methods known to one skilled in the art. Several different coating methods may be employed such as spray coating, pan coating, fluid bed coating, spin coating, or roll coating. Other methods may be used.

In some embodiments, coating may refer to associations that are transient, or in another embodiment, may be permanent. In one embodiment, association is by means of chemical conjugation or via physical entrapment. Coating may result of both chemical conjugation and physical entrapment. Such associations may be via covalent bonding, or ionic bonding, hydrophobic interactions, via Van Der Waal's forces, etc., or any appropriate interaction, as will be appreciated by one skilled in the art.

Additional coating materials may be applied to further support coating 27, The coating of the in-vivo device 20 with a chemical compound may employ the use of adhesive compounds which promote and/or support coating of the in-vivo device 20. The coating of the in-vivo device 20 may make use of other materials which facilitate or promote such coating, such as, for example, the use of fillers, disintegrants, stabilizers, and others, as will be appreciated by one skilled in the art.

In one embodiment, coating 27 may include a body lumen clearing agent, wherein the agent or compound may be incorporated within a matrix, which is applied to a portion of a surface of in-vivo device 20 housing. Such adsorption may affect the release rate of the compound, so as to promote immediate release, or release over an extended period. The coating may be pH sensitive thus allowing the release of the chemical compound in a pre-defined pH range. Another embodiment of the invention provides that the coating includes compounds so adsorbed as to be surface exposed on the applied region of the in-vivo device 20.

In some embodiments, the in-vivo device 20 may be coated with a polymer and thus form coating 27. The choice of polymer may affect the release kinetics of the compound or affect the surface characteristics of the in-vivo device 20 to suit a desired application. The polymer may be for example polyethylene terephthalate, polyurethane poly (hydroxymethyl-p-xylylene-co-p-xylylene), polylactic acid, parylene, fibrin, polytetrafluoroethylene, polyamide, polystyrene, polydimethylsiloxane, polyoxymethylene, polyacrylonitrile, polytetrafluoroethylene, polycarbonate, polyetheramide, polyvinylidine, polyester, polyethylcyanoacrilate or polyamine. Other suitable polymers may be used.

In some embodiments, the body lumen clearing element may be present within the in-vivo device 20 housing. For example body lumen clearing agent may be present In reservoir 28 in the in-vivo device 20. A body lumen clearing element contained in in-vivo device 20 housing may be present in a liquid form or in a solid form. The reservoir 28 may be sealed with coating or plug materials that avow different release profiles as will be suitable for a given application.

The administration of the in-vivo device 20 and a composition containing a lumen clearing element may be via the oral route.

In some embodiments, device 20 may not be a capsule shaped in-vivo device, but may be an endoscope, a catheter or other in-vivo devices comprising a lumen clearing agent connected to the in-vivo device's housing. The lumen clearing agent may either be coated on the in-vivo device's housing or may be within the in-vivo device's housing.

Figure 3:
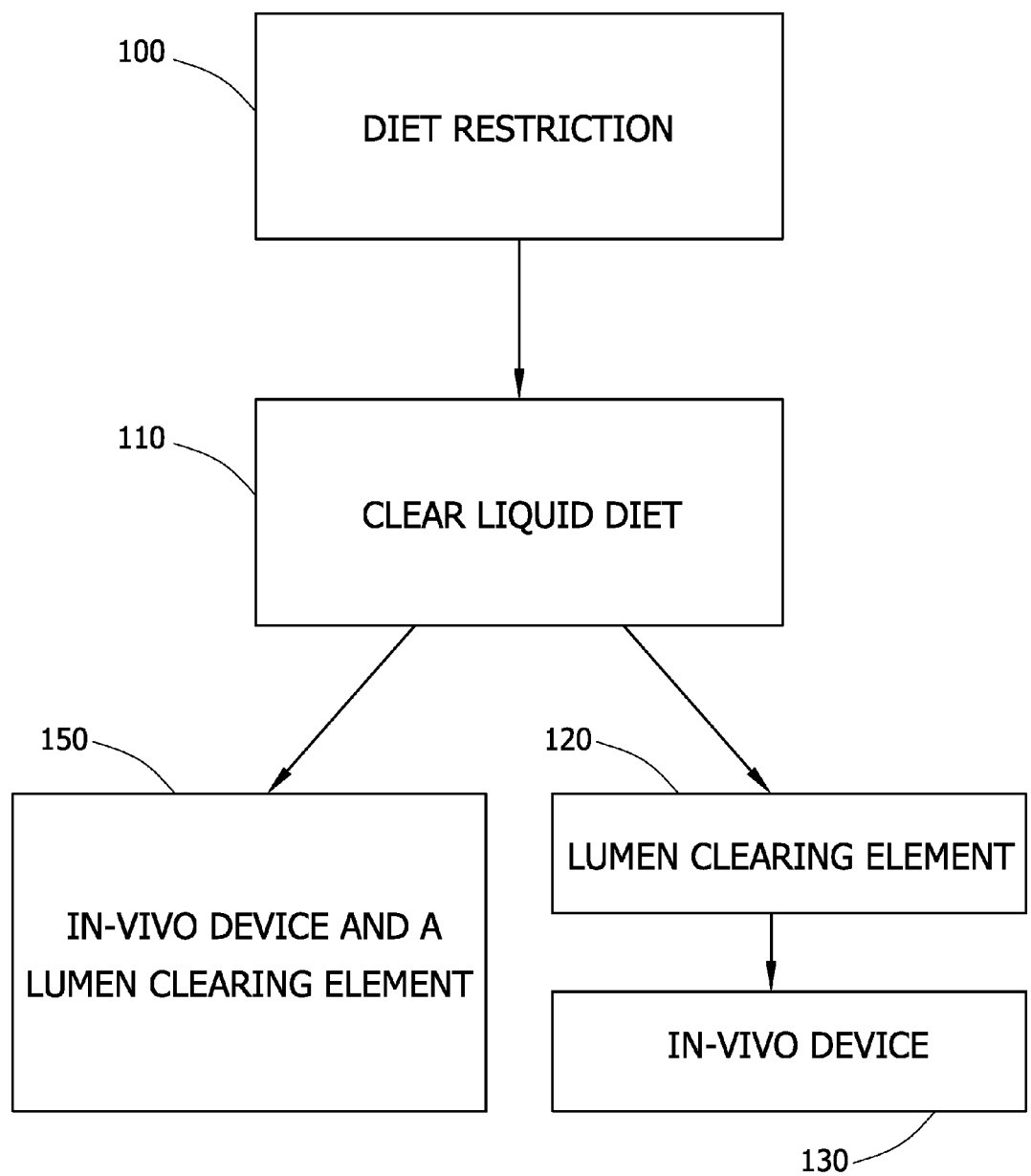
FIG. 3 illustrates a series of operations of a method according to an embodiment of the invention.

FIG. 3 depicts a method of in-vivo viewing according to one embodiment of the invention. In one embodiment, in operation 100 a patient may be placed on a diet restricted to liquids or foods that provide a minimal colonic fecal residue beginning, for example, 1-5 days prior to administering the composition containing a lumen clearing element and an in-vivo device 20. In operation 110, the patient may be restricted to a clear liquid diet, for example, 16-48 hours prior to administering the composition containing a lumen clearing element and an in-vivo device 20. In operation 120, administration of a composition containing a lumen clearing element may take place. In operation 130, administering to a subject of an in-vivo sensing or imaging device such as, for example, in-vivo device 20, may take place. In place of operations 120 and 130, in operation 150, an in-vivo device which includes a lumen clearing element may be administered, for example by inserting or swallowing. Other steps or series of steps may take place. Other time limits or time frames may be used.

According to some embodiments a method for clearing a subject's body lumen, such as parts of the GI tract, is provided. Typically this embodiment includes operations 100-120 described above but need not include administration of an in vivo sensing or imaging device. Methods for clearing a body lumen according to embodiments of the invention may be used in connection with other procedures, not necessarily using an in vivo imaging or sensing device. For example, a method for clearing a subject's body lumen may be used prior to a radiological exam using an imaging modality such as CT.

In one embodiment, the in-vivo device 20 and the composition containing a lumen clearing element are administered simultaneously and/or in a single dosage form including both the in-vivo device 20 and the composition containing a lumen clearing element as described herein. The single dosage firm may contain additional materials.

In one embodiment, the oral dosage form includes a predefined release profile. Predefined release profile, may include, for example an extended release profile, slow release profile, or an immediate release profile. Release profile may be, for example, pH-dependent or dependent on the type of coating, e.g. enteric coating, which may result in release occurring in the gastrointestinal tract. The oral dosage form may be formulated according to the desired release profile of the pharmaceutical active ingredient and/or according to the procedure as known to one skilled in the art.

According to one embodiment, a method of clearing a body lumen may include the administration of an in-vivo device 20 and a composition containing a lumen clearing element in two or more discrete dosage forms. When administering a composition containing a lumen clearing element followed by the administration/insertion of an in-vivo device 20, the dosing regimen may vary and the period of time, between administering a composition containing a lumen clearing element and administering an in-vivo device may range from seconds to days, as will be suitable for a given application. Each dose of the lumen clearing agent may have a different composition, suitable for the anticipated lumen content characteristics at the stage it is administered.

The in-vivo device may be administered following administration of a composition containing a lumen clearing element that may be formulated for example as a tablet, capsule, lozenge, powder, granule, caplet, solution, suspension, emulsion or a combination thereof. Other administration methods may be used.

A method according to some embodiments may include more than a single dose of a lumen clearing element. The actual dosing regimen is designed to suit a given application.

According to some embodiments, a method may comprise administration of a composition comprising a lumen clearing agent of a certain dose prior to insertion of an in-vivo device. In some embodiments, there may be administration of another composition comprising a lumen clearing agent of a different dose subsequent to the insertion of the device.

In other embodiments, the administration of a composition prior to insertion of an in-vivo device, may be of a composition comprising a certain coagulant, flocculant, aggregant, or a combination thereof, whereas the composition administered subsequent to the device's insertion may be of a composition comprising a different coagulant, flocculant, aggregant or a combination thereof. In other embodiments, there may be different release profiles between compositions, or any combination of dose, chemical composition and/or release profile.

A method according to some embodiments may include gut lavage in the form of saline or balanced electrolyte solutions. Gut lavage solutions may, in some embodiments, be administered orally or by nasogastric tube. In some embodiments, saline or balanced electrolyte solutions may be administered in amounts varying from for example 6 L to 12 L.

Peroral compositions may include for example liquid solutions, emulsions, suspensions, and the like. The pharmaceutically-acceptable carriers suitable for preparation of such compositions are well known in the art.

In one embodiment, the gut lavage solution is polyethylene glycol-electrolyte lavage solution (PEG-ELS). Another embodiment of the invention provides that the gut lavage solution is sulphate free polyethylene glycol-electrolyte lavage solution (SF-ELS). PEG-ELS or SF-ELS may, in some embodiments, be formulated as tablets. In some embodiments, 15-60 tablets are taken with 5-30 10-oz glasses of water. Other dosages that may fit a given application may be used.

In some embodiments oral sodium phosphate or sodium picosulphate may be utilized as a lavage solution. Pharmaceutical preparations of oral sodium phosphate may contain for example 300-400 mmol monobasic sodium phosphate and 100-150 mmol dibasic sodium phosphate in 90 mL water. The dosing regimen of oral sodium phosphate or sodium picosulphate preparation may be for example 1-3 times, prior to the procedure. Sodium phosphate monobasic, monohydrate and sodium phosphate dibasic, anhydrous or sodium picosulphate also known as Magnesium citrate may, in some embodiments, be formulated as tablets. In some embodiments, 15-60 tablets are taken with 5-30 10-oz glasses of water.

In some embodiments, senna may be formulated as tablets which contain for example 8-20 mg of sennoside A, sennoside B, or a combination thereof. A dose of 10-40 tablets may be administered with 5-15 10-oz glasses of water. Other dosages and amounts may be used.

Flavoring agents may be added for improvement of palatability. The amount and type of the flavoring agents to be added will be readily understood by those skilled in the art. Palatability may also be increased by chilling the solution prior to administration.

Some embodiments may further include adjuncts. Magnesium citrate, bisacodyl, metoclopramide, senna, or a combination thereof may be used to facilitate a clearance of a body lumen.

In some embodiments, adjuncts may be administered in various formulations as known to one skilled in the art up to for example 5 days prior to the procedure.

Simethicine may be used, in one embodiment, to reduce the formation of bubbles seen during colonoscopy, while, charcoal may be used to reduce gasses prior to and during colonoscopy.

The term "clearing" as used herein may refer to cleansing, removing or neutralizing content which may reduce image quality, reducing turbidity, decontaminating, refining, or a combination thereof.

The term "procedure" as used herein may refer in one embodiment to a viewing a body lumen using, for example, an in-vivo imaging device. The term "procedure" may refer to colonoscopy or other in-vivo viewing wherein the in-vivo device or a similar device is used.

In some embodiments, clearing a body lumen may include, clearing the colon lumen; in such case the body lumen clearing element is a colon lumen clearing element. Colon lumen clearing element may act via separation of solid luminal contents from the luminal fluids.

In some embodiments, a lumen clearing element may include, for example biocompatible mechanical particles such as liposomes, plastic particles, e.g. plastic balls, etc. The surface of the particles may, in some embodiments, have a negative or positive charge. The particle surface may be hydrophilic. The particles may spread evenly once they enter a body lumen while adsorbing the contents spread throughout a body lumen. In other embodiments, the particles may be packaged to delay their dispersion to occur at a target area, such as the colon lumen.

In some embodiments, a lumen clearing element may include particles (e.g. porous beads, on Exchange Resins and/or other flocculants or coagulants) in various shapes, electric charges and specific gravities in order to optimize dispersion along the lumen.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of reducing turbidity of a fluid within at least a portion of a gastrointestinal tract for the purpose of imaging therein, said method comprising:
   separating solid luminal particles from luminal fluids within the fluid in at least said portion of the gastrointestinal tract by administering into at least said portion of the gastrointestinal tract a composition containing a turbidity reducing element, without removing the fluid from at least said portion of the gastrointestinal tract, said turbidity reducing element comprising an element selected from the group consisting of: a coagulant, a flocculant, an aggregant, and a combination thereof,
      wherein administration of said turbidity reducing element in said composition reduces the turbidity of the fluid within at least said portion of the gastrointestinal tract so as to enable clear imaging therein.

2. The method according to claim 1, wherein said step of administering said composition containing the turbidity reducing element comprises administering the composition in two or more discrete dosage forms.

3. The method according to claim 1, wherein said turbidity reducing element is in a form selected from the group consisting of: a tablet, capsule, lozenge, powder, granule, caplet, solution, suspension, emulsion, or a combination thereof.

4. The method according to claim 1, wherein said method further comprises the step of administering a clear liquid diet, prior to the step of administering the composition containing the turbidity reducing element.

5. The method according to claim 1, wherein said method further comprises the step of inserting an in-vivo device into at least the portion of the gastrointestinal tract, following administering the composition containing the turbidity reducing element.

6. The method according to claim 5, wherein said in-vivo device is selected from the group consisting of: a swallowable imaging capsule, an endoscope, a colonoscope, and other intra luminal viewing and imaging devices.

7. The method according to claim 1, wherein said method further comprises the step of administering gut-lavage solutions.

8. The method according to claim 1, wherein at least said portion of the gastrointestinal tract is a colon.

9. The method according to claim 1, wherein said turbidity reducing element is contained in an in-vivo device.

10. The method according to claim 9, wherein said turbidity reducing element is incorporated within a coating coated on a surface of the in-vivo device.

11. The method according to claim 9, wherein said in-vivo device comprises a cavity or reservoir sized to contain said composition and is configured to release said composition from said cavity or reservoir into at least said portion of the gastrointestinal tract.

12. The method according to claim 11, wherein said composition is released from said cavity or reservoir into at least the portion of the gastrointestinal tract by a valve, a pump or a dissolvable plug.

13. The method according to claim 1, wherein said step of administering the composition containing the turbidity reducing element comprises inserting an in-vivo device into at least the portion of the gastrointestinal tract, said in-vivo device having a cavity or reservoir sized to contain said composition and being configured to release said composition into at least the portion of the gastrointestinal tract.

14. The method according to claim 13, wherein said composition is released from said cavity or reservoir into at least the portion of the gastrointestinal tract by a valve, a pump or a dissolvable plug.

* * * * *